US012758099B2

(12) United States Patent
Chen et al.

(10) Patent No.: US 12,758,099 B2
(45) Date of Patent: Oct. 13, 2026

(54) OPTICAL BIOMEDICAL MEASUREMENT DEVICE

(71) Applicant: Taiwan-Asia Semiconductor Corporation, Hsinchu City (TW)

(72) Inventors: Chun-Ko Chen, Hsinchu City (TW); Tzu-Hui Lin, Hsinchu City (TW)

(73) Assignee: Taiwan-Asia Semiconductor Corporation, Hsinchu City (TW)

(*) Notice: Subject to any disclaimer, the term of this patent is extended or adjusted under 35 U.S.C. 154(b) by 71 days.

(21) Appl. No.: 18/671,557

(22) Filed: May 22, 2024

(65) Prior Publication Data

US 2025/0134376 A1 May 1, 2025

(30) Foreign Application Priority Data

Oct. 26, 2023 (TW) ................................ 112141070

(51) Int. Cl.
*A61B 5/00* (2006.01)
*A61L 31/02* (2006.01)
(Continued)

(52) U.S. Cl.
CPC ............ *A61B 5/0059* (2013.01); *A61B 5/681* (2013.01); *A61L 31/022* (2013.01); *A61L 31/16* (2013.01);
(Continued)

(58) Field of Classification Search
CPC ............ G02B 2207/101; G02B 6/0073; G01N 2015/1493; G01N 15/1434;
(Continued)

(56) References Cited

U.S. PATENT DOCUMENTS

2010/0316078 A1* 12/2010 Ono ..................... G01N 21/554
372/45.01
2011/0024627 A1* 2/2011 Yao ....................... G01J 1/0271
250/353
(Continued)

FOREIGN PATENT DOCUMENTS

CN 2920250 Y 7/2007
CN 101433729 A 5/2009
(Continued)

OTHER PUBLICATIONS

S H Mohamed et al., "Thickness and annealing effects on the optoelectronic properties of ZnS films", Journal of Physics D: Applied Physics 43, Feb. 3, 2010, pp. 1-7.
(Continued)

*Primary Examiner* — Gerald Johnson
(74) *Attorney, Agent, or Firm* — MUNCY, GEISSLER, OLDS & LOWE, P.C.

(57) ABSTRACT

An optical biomedical measurement device is provided. The optical biomedical measurement device includes a substrate, a light source disposed on the substrate, a photodiode sensor disposed on the substrate, laterally spaced from the light source, a plurality of light-blocking walls disposed vertically on the substrate, laterally located on both sides of the light source and on both sides of the photodiode sensor, a sealing layer covering the light source, the photodiode sensor, and the light-blocking walls, a cover plate bonded to the sealing layer, a plurality of light-absorption films vertically aligned with the light-blocking walls, disposed in a plurality of etching regions on a top surface of the cover plate, an optical filter film disposed on the cover plate and the light-absorption films, a plurality of nano-metal particles arranged on the optical filter film with a distance therebetween, and an
(Continued)

100 antibacterial optical film covering the nano-metal particles and the optical filter film.

12 Claims, 4 Drawing Sheets

(51) Int. Cl.
*A61L 31/16* (2006.01)
*G02B 1/18* (2015.01)
*G02B 5/20* (2006.01)

(52) U.S. Cl.
CPC ........ *G02B 1/18* (2015.01); *A61B 2560/0462* (2013.01); *A61B 2562/0238* (2013.01); *A61B 2562/185* (2013.01); *A61L 2300/104* (2013.01); *A61L 2300/404* (2013.01); *A61L 2400/12* (2013.01); *G02B 5/206* (2013.01); *G02B 2207/101* (2013.01)

(58) Field of Classification Search
CPC .......... G01N 2021/3181; G01N 21/554; A61B 2562/0238; A61B 5/681; A61B 2560/0462; A61B 5/14532; A61B 5/024; A61B 5/021; A61K 33/38; G02F 1/1333; A61F 2002/3084
See application file for complete search history.

(56) References Cited

U.S. PATENT DOCUMENTS

| | | | | |
|---|---|---|---|---|
| 2016/0238440 | A1 | 8/2016 | Chu et al. | |
| 2017/0219818 | A1* | 8/2017 | Fang | G02B 5/3083 |
| 2019/0090766 | A1* | 3/2019 | Block | A61B 5/02433 |
| 2020/0343385 | A1* | 10/2020 | Zan | H01L 21/02565 |
| 2022/0132859 | A1 | 5/2022 | Sowwan et al. | |
| 2023/0093839 | A1* | 3/2023 | Gao | G02B 3/0012 |

FOREIGN PATENT DOCUMENTS

| | | | | |
|---|---|---|---|---|
| CN | 104609029 | A | 5/2015 | |
| CN | 110579829 | A | 12/2019 | |
| CN | 211443322 | U | 9/2020 | |
| CN | 211786834 | U | 10/2020 | |
| CN | 113322431 | A | 8/2021 | |
| CN | 113711270 | A | 11/2021 | |
| CN | 115610052 | A * | 1/2023 | B32B 27/308 |
| CN | 115657190 | A | 1/2023 | |
| CN | 116394618 | A * | 7/2023 | B32B 27/36 |
| EP | 1609826 | A2 * | 12/2005 | C09D 5/14 |
| JP | 2003316504 | A | 11/2003 | |
| JP | 2005160641 | A | 6/2005 | |
| JP | WO2009031344 | A1 * | 12/2010 | B82Y 10/00 |
| JP | 2015074672 | A * | 4/2015 | |
| KR | 1020140118065 | A | 10/2014 | |
| KR | 102074698 | B1 | 2/2020 | |
| KR | 102162521 | B1 * | 10/2020 | C09J 7/385 |
| KR | 102332025 | B1 | 12/2021 | |
| TW | 201230404 | A | 7/2012 | |
| TW | 201327958 | A1 | 7/2013 | |
| TW | 201630838 | A | 9/2016 | |

OTHER PUBLICATIONS

Yiming Bai et al., "Tailoring film agglomeration for preparation of silver nanoparticles with controlled morphology", Materials and Design 103 (2016), pp. 315-320.
S. Vijayan et al., "Investigation of Structural, Optical and Antibacterial Activity of ZnS Nanoparticles", Journal of Cluster Science (2021) 32, pp. 1601-1608, Published online Nov. 1, 2020.

* cited by examiner

OPTICAL BIOMEDICAL MEASUREMENT DEVICE

CROSS-REFERENCES TO RELATED APPLICATIONS

This application claims priority to Taiwan Patent Application No. 112141070 filed on Oct. 26, 2023, which is hereby incorporated by reference in its entirety.

BACKGROUND OF THE INVENTION

Field of the Invention

The present invention relates to an optical biomedical measurement device, particularly to a non-invasive optical biomedical measurement device.

Descriptions of the Related Art

In recent years, smart wearable devices (e.g., smart watches, etc.) have become popular. They can be used as non-invasive optical biomedical measurement devices to provide users with various physiological information (e.g., heart rate, blood oxygen saturation, blood pressure, blood glucose, etc.).

Due to the prolonged wear of the device against the body and its exposure to sweat from the surface of human skin, these contact areas are likely to become breeding grounds for bacteria. As these contact areas rub against the human skin over time, these bacteria may enter the skin and cause infections such as abscesses or painful rashes.

Given this, how to enhance the antibacterial ability of wearable devices is an urgent issue for the industry to solve.

SUMMARY OF THE INVENTION

An objective of the present invention is to improve the antibacterial ability of an optical biomedical measurement device. The present invention achieves the effect of enhancing the antibacterial ability by improving the process of forming the antibacterial optical film to make the antibacterial optical film has a periodic nano-structure for increasing the surface area (i.e., reaction area) of the antibacterial optical film. Accordingly, compared with conventional wearable devices, the wearable device using the optical biomedical measurement device of the present invention can have higher antibacterial ability.

To achieve the above objective, the present invention discloses an optical biomedical measurement device which includes: a substrate, a light source disposed on the substrate, a photodiode sensor disposed on the substrate, laterally spaced from the light source, a plurality of light-blocking walls disposed vertically on the substrate, laterally located on both sides of the light source and on both sides of the photodiode sensor, a sealing layer covering the light source, the photodiode sensor, and the light-blocking walls, a cover plate bonded to the sealing layer, a plurality of light-absorption films vertically aligned with the light-blocking walls, disposed in a plurality of etching regions on a top surface of the cover plate, an optical filter film disposed on the cover plate and the light-absorption films, a plurality of nano-metal particles arranged on the optical filter film with a distance therebetween, and an antibacterial optical film covering the nano-metal particles and the optical filter film.

In an example, the nano-metal particles are a plurality of nano-silver particles.

In an example, a ratio of an area of the nano-silver particles to an area of the optical filter film is less than 10%.

In an example, the nano-silver particles have a particle diameter of less than 5 nanometers (nm).

In an example, the distance of the nano-silver particles from each other is 50 nm to 100 nm.

In an example, the nano-silver particles are formed by performing a thermal annealing process after forming a silver film on the optical filter film.

In an example, the thermal annealing process is performed at 300° C. to 500° C. for 60 minutes.

In an example, a thickness of the antibacterial optical film is greater than 5 nm.

In an example, the antibacterial optical film has a refractive index of 1.5 to 2.5.

In an example, the antibacterial optical film is made of zinc sulfide material.

In an example, the light source is a light-emitting diode.

In an example, the optical filter film is formed by interleavedly stacking a plurality of titanium dioxide layers and a plurality of silicon dioxide layers.

After referring to the drawings and the detailed description of embodiments described later, those of ordinary skill in the art can understand other objectives of the present invention, as well as the technical means and implementations of the present invention.

BRIEF DESCRIPTION OF THE DRA WINGS

DETAILED DESCRIPTION OF THE PREFERRED EMBODIMENT

In the following description, the present invention will be explained with reference to various embodiments thereof. These embodiments of the present invention are not intended to limit the present invention to any specific environment, application or particular method for implementations described in these embodiments. Therefore, the description of these embodiments is for illustrative purposes only and is not intended to limit the present invention. It shall be appreciated that, in the following embodiments and the attached drawings, partial elements not directly related to the present invention are omitted from the illustration, and dimensional proportions among individual elements and the numbers of each element in the accompanying drawings are provided only for ease of understanding but are not intended to limit the actual scale.

Figure 1:
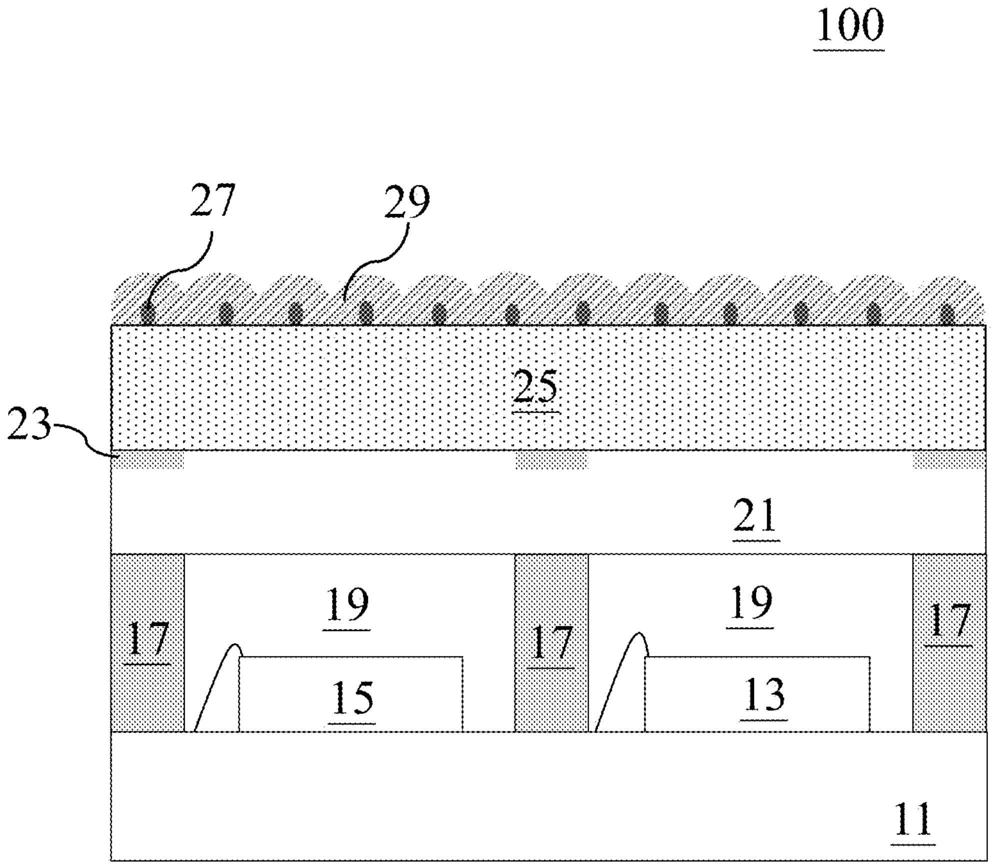
FIG. 1 is a schematic cross-sectional view of an optical biomedical measurement device according to an embodiment of the present invention.

An embodiment of the present invention is shown in FIG. 1, which is a schematic cross-sectional view of an optical biomedical measurement device 100. The optical biomedical measurement device 100 may be used, for example, to measure blood glucose, but is not limited thereto. In other embodiments, by adjusting the applied spectral ranges, the optical biomedical measurement device of the present invention may also be used to measure other physiological information (e.g., heart rate, blood oxygen saturation, blood pressure, etc.).

The optical biomedical measurement device 100 includes a substrate 11, a light source 13, a photodiode (PD) sensor 15, a plurality of light-blocking walls 17, a sealing layer 19, a cover plate 21, a plurality of light-absorption film 23, an optical filter film 25, a plurality of nano-metal particles 27 and an antibacterial optical film 29.

The substrate 11 may be a ceramic circuit board, but is not limited thereto. The thickness of the substrate 11 may be 0.45 millimeters (mm), but is not limited thereto. The light source 13 is disposed on the substrate 11. The light source 13 may be a light-emitting diode, e.g., a light-emitting diode generating light with a wavelength of 700 nm to 2000 nm. In other embodiments, the light source 13 may be another light-emitting device generating light in a specific wavelength range.

The photodiode sensor 15 is also disposed on the substrate 11 and is laterally spaced apart from the light source 13. The photodiode sensor 15 may be an indium gallium arsenide (InGaAs) photodiode sensor whose light-sensing wavelength range is 900 nm to 1700 nm, but is not limited thereto. The light-blocking walls 17 (e.g., three light-blocking walls) are arranged vertically on the substrate 11 and are laterally located on both sides of the light source 13 and both sides of the photodiode sensor 15. The light-blocking walls 17 can ensure that the light emitted from the light source 13 is not directly received by the photodiode sensor 15 and can also prevent light leakage. For example, each light-blocking wall 17 can be made of epoxy resin, which has a matte black appearance after curing so that neither visible light nor invisible light can penetrate each light-blocking wall 17. The height of the light-blocking walls 17 may be 0.5 mm, but is not limited thereto.

The sealing layer 19 may be a transparent epoxy resin, which covers the light source 13, the photodiode sensor 15 and the light-blocking walls 17, and allows the cover plate 21 to be bonded to the sealing layer 19. The cover plate 21 may be made of glass material. The thickness of the cover plate 21 may be 0.4 mm, but is not limited thereto. The light-absorption films 23 are vertically aligned with the light-blocking walls 17 and are disposed in a plurality of etched areas on a top surface of the cover plate 21. The light-absorption films 23 are used to absorb unnecessary reflected light.

Specifically, the etched areas are first formed on the top surface of the cover plate 21 at positions directly aligned with the light-blocking walls 17 by an etching process, and then the light-absorption films 23 are formed in the etched areas. Each light-absorption film 23 may be formed by interleavedly stacking a plurality of chromium (Cr) layers and a plurality of silicon dioxide ($SiO_2$) layers, and has the characteristics of low reflection and high absorption. The thickness of each light-absorption film 23 may be 500 nm to 1500 nm. The thickness of each light-absorption film 23 is preferably 960 nm.

The optical filter film 25 is disposed on the cover plate 21 and the light-absorption films 23 to allow light within a specific spectrum to penetrate and reflect light within other spectra. The thickness of the optical filter film 25 may be 4 micrometers (μm)–10 μm. The thickness of the optical filter film 25 is preferably 4 μm. For example, the optical filter film 25 may be formed by interleavedly stack a plurality of titanium dioxide layers and a plurality of silicon dioxide layers, and may be formed by a physical vapor deposition (PVD) method or achemical vapor deposition (CVD) method. The thickness of each titanium dioxide layer and each silicon dioxide layer can be determined based on the wavelength of light, that is, based on the spectrum of the light source 13.

Figure 2:
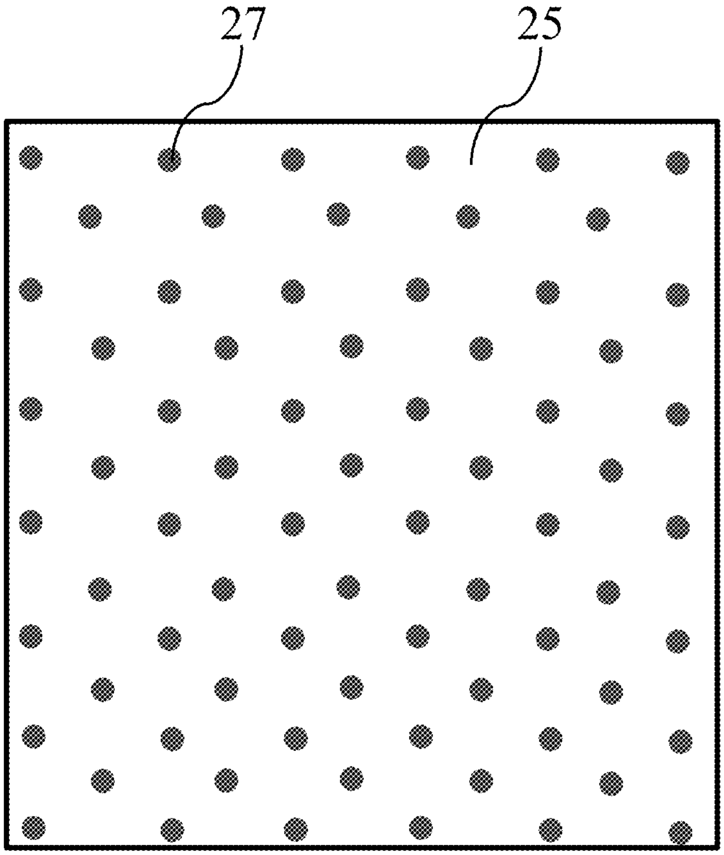
FIG. 2 is a schematic top view illustrating a plurality of nano-metal particles formed on the optical filter film.

The nano-metal particles 27 are arranged on the optical filter film 25 with a distance therebetween. As shown in FIG. 2, the nano-metal particles 27 are periodically arranged on the optical filter film 25. It should be noted that the pattern of the nano-metal particles 27 shown in FIG. 2 is only illustrative and not limited thereto. In other words, the nano-metal particles 27 may be configured to present any periodically arranged pattern and these possible patterns all fall within the scope of the present invention.

For example, the nano-metal particles 27 may be a plurality of nanosilver particles to further provide an antibacterial effect. The ratio of the area of the nano-silver particles to the area of the optical filter film 25 may be less than 10%. The nano-silver particles have a particle diameter of less than 5 nanometers (nm). The distance of the nano-silver particles from each other may be 50 nm to 100 nm. In an embodiment, the particle diameter of the nano-silver particles is 5 nm, the distance between them is 50 nm (i.e., the period is 50 nm), and the ratio of the area of the nano-silver particles to the area of the optical filter film 25 is 8%.

Figure 3A:
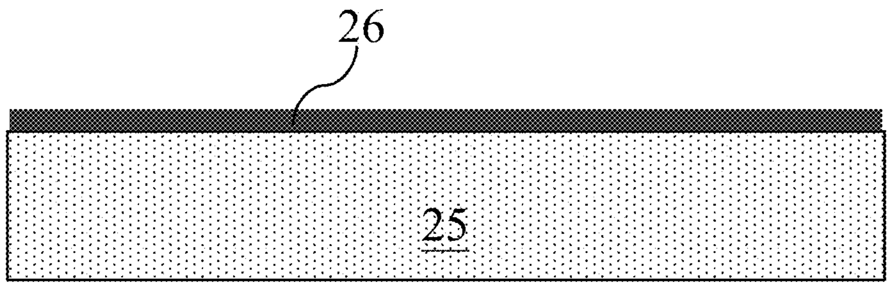
FIGS. 3A and 3B are schematic views illustrating the process of forming a plurality of nano-metal particles on the optical filter film.
Figure 3B:
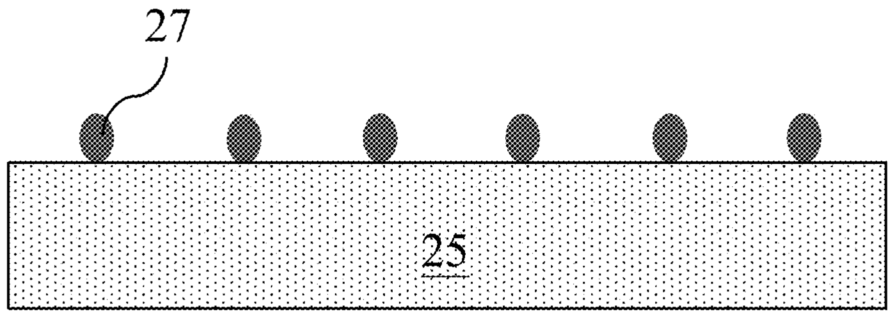

FIGS. 3A and 3B show practical examples of the formation of such nano-metal particles 27 (here, nano-silver particles are used for illustration). First, a silver film 26 is formed on the optical filter film 25 (e.g., by a physical vapor deposition method) as shown in FIG. 3A. Then, a thermal annealing process is performed to form the nano-metal particles 27, as shown in FIG. 3B. For example, the thermal annealing process may be performed at 300° C. to 500° C. for 60 minutes so that the silver film 26 is clustered into a periodic nano-particle structure. The particle diameter of the nano-metal particles 27 will change corresponding to the thickness of the silver film 26. Therefore, in practice, the particle diameter of the nano-metal particles can be changed by adjusting the thickness of the silver film 26.

The antibacterial optical film 29 covers the nano-metal particles 27 and the optical filter film 25. The antibacterial optical film 29 is in contact with human skin when the optical biomedical measurement device 100 is in use. The antibacterial optical film 29 may be made of zinc sulfide (ZnS) material, but is not limited thereto. In addition, in practice, the thickness of the antibacterial optical film 29 may be greater than 5 nm, and the refractive index of the antibacterial optical film 29 may be 1.5 to 2.5, but is not limited thereto. In other words, the periodic nano-structure (i.e., the optical filter film 25 on which the nano-metal particles 27 are arranged) may be plated with a zinc sulfide layer having a thickness greater than 5 nm.

It should be noted that in the present invention, the cover plate 21 and the structure above it may be made into a module first. In other words, the present invention may first form the light-absorption films 23 in the etched areas of the cover plate 21, and then form the optical filter film 25 on the cover plate 21 and the light-absorption films 23. Then, the nano-metal particles 27 and the antibacterial optical film 29 are formed on the optical filter film 25 to produce the module. Finally, the module is bonded to the sealing layer 19 (i.e., the cover plate 21 is bonded to the sealing layer 19) to complete the optical biomedical measurement device 100 of the present invention. In an embodiment, the present invention may use a large cover plate, form the aforementioned structure thereon, and obtain multiple modules by cutting.

Figure 4A:
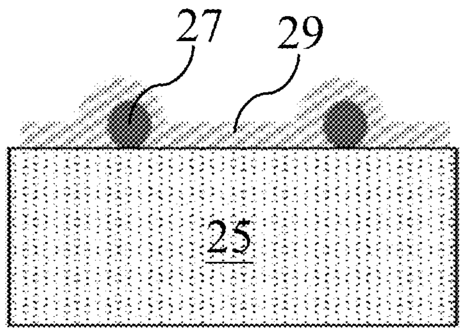
FIGS. 4A and 4B are schematic views respectively showing the embodiments of antibacterial optical films with different thicknesses.
Figure 4B:
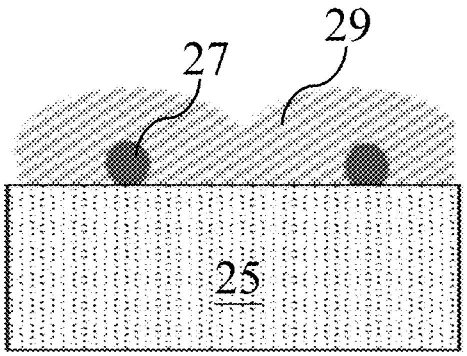

FIGS. 4A and 4B, respectively, depict the implementations of the antibacterial optical films 29 with different thicknesses. It is assumed the conditions that the particle diameter of these nano-metal particles 27 (here, nano-silver particles are used for illustration) is 5 nm and the period is 50 nm. When the thickness of the antibacterial optical film 29 is 5 nm, the surface area of the antibacterial optical film 29 can be increased by about 17% (as shown in FIG. 4A), compared with that of the conventional flat antibacterial optical film. When the thickness of the antibacterial optical film 29 is 25 nm, the surface area of the antibacterial optical film 29 can be increased by about 70% (as shown in FIG. 4B), compared with that of the conventional flat antibacterial optical film. Therefore, compared with the surface area of the conventional flat antibacterial optical film, the surface area of the antibacterial optical film 29 of the present invention can be increased by about 17% to 70%. In addition, based on the practical results, the thickness of the antibacterial optical film 29 of the present invention is preferably 25 nm.

In summary, the present invention forms periodically arranged nano-metal particles on the optical filter film to make the antibacterial optical film formed later also have a periodic nano-structure. Accordingly, the present invention can effectively increase the surface area (i.e., reaction area) of the antibacterial optical film and thereby improve the antibacterial ability of the wearable device.

The above embodiments are used only to illustrate the implementations of the present invention and to explain the technical features of the present invention, and are not intended to limit the scope of the present invention. Any modifications or equivalent arrangements that can be easily accomplished by those skilled in this art are considered to fall within the scope of the present invention, and the scope of the present invention should be limited by the claims of the patent application.

What is claimed is:

1. An optical biomedical measurement device, comprising:
- a substrate;
- a light source disposed on the substrate;
- a photodiode sensor disposed on the substrate, laterally spaced from the light source;
- a plurality of light-blocking walls disposed vertically on the substrate, laterally located on both sides of the light source and on both sides of the photodiode sensor;
- a sealing layer covering the light source, the photodiode sensor, and the light-blocking walls;
- a cover plate bonded to the sealing layer;
- a plurality of light-absorption films vertically aligned with the light-blocking walls, disposed in a plurality of etching regions on a top surface of the cover plate;
- an optical filter film disposed on the cover plate and the light-absorption films;
- a plurality of nano-metal particles periodically arranged on the optical filter film with a distance therebetween; and
- an antibacterial optical film covering the nano-metal particles and the optical filter film, whereby the antibacterial optical film has a periodic nano-structure for increasing a surface area of the antibacterial optical film.

2. The optical biomedical measurement device of claim 1, wherein the nano-metal particles are a plurality of nano-silver particles.

3. The optical biomedical measurement device of claim 2, wherein a ratio of an area of the nano-silver particles to an area of the optical filter film is less than 10%.

4. The optical biomedical measurement device of claim 2, wherein the nano-silver particles have a particle diameter of less than 5 nanometers (nm).

5. The optical biomedical measurement device of claim 2, wherein the distance of the nano-silver particles therebetween is 50 nm to 100 nm.

6. The optical biomedical measurement device of claim 2, wherein the nano-silver particles are formed by performing a thermal annealing process after forming a silver film on the optical filter film.

7. The optical biomedical measurement device of claim 6, wherein the thermal annealing process is performed at 300° C. to 500° C. for 60 minutes.

8. The optical biomedical measurement device of claim 1, wherein a thickness of the antibacterial optical film is greater than 5 nm.

9. The optical biomedical measurement device of claim 1, wherein the antibacterial optical film has a refractive index of 1.5 to 2.5.

10. The optical biomedical measurement device of claim 1, wherein the antibacterial optical film is made of zinc sulfide material.

11. The optical biomedical measurement device of claim 1, wherein the light source is a light-emitting diode.

12. The optical biomedical measurement device of claim 1, wherein the optical filter film is formed by interleavedly stacking a plurality of titanium dioxide layers and a plurality of silicon dioxide layers.

* * * * *